(12) United States Patent
Kameshima

(10) Patent No.: US 7,271,391 B2
(45) Date of Patent: Sep. 18, 2007

(54) RADIOGRAPHIC IMAGING APPARATUS AND SYSTEM, METHOD THEREFOR, AND PROGRAM

(75) Inventor: Toshio Kameshima, Kumagaya (JP)

(73) Assignee: Canon Kabushiki Kaisha, Tokyo (JP)

( * ) Notice: Subject to any disclaimer, the term of this patent is extended or adjusted under 35 U.S.C. 154(b) by 106 days.

(21) Appl. No.: 11/240,081

(22) Filed: Sep. 29, 2005

(65) Prior Publication Data
US 2006/0071171 A1    Apr. 6, 2006

(30) Foreign Application Priority Data
Oct. 1, 2004    (JP) .................... 2004-290655

(51) Int. Cl.
*H01L 27/146* (2006.01)
(52) U.S. Cl. ................................. 250/370.09
(58) Field of Classification Search ............ 250/370.09
See application file for complete search history.

(56) References Cited

U.S. PATENT DOCUMENTS

| | | | |
|---|---|---|---|
| 5,079,426 A | 1/1992 | Antonuk et al. | |
| 5,677,940 A | 10/1997 | Suzuki et al. | |
| 6,515,286 B2 | 2/2003 | Kuwabara | |
| 7,039,162 B2* | 5/2006 | Ikeda et al. ............... | 378/98.8 |
| 2001/0038076 A1 | 11/2001 | Kuwabara .............. | 250/370.11 |
| 2002/0050568 A1 | 5/2002 | Nonaka ................. | 250/370.09 |
| 2002/0121606 A1* | 9/2002 | Okada et al. .......... | 250/370.11 |
| 2003/0194058 A1 | 10/2003 | Tsujii ..................... | 378/210 |
| 2005/0023476 A1* | 2/2005 | Haas et al. ............. | 250/370.11 |

FOREIGN PATENT DOCUMENTS

| | | |
|---|---|---|
| EP | 1 441 237 | 7/2004 |
| JP | 08-130682 | 5/1996 |
| JP | 11151233 A * | 6/1999 |

OTHER PUBLICATIONS

European Search Report for corresponding European Application No. 05 02 1333.

* cited by examiner

*Primary Examiner*—David Porta
*Assistant Examiner*—Mindy Vu
(74) *Attorney, Agent, or Firm*—Morgan & Finnegan L.L.P.

(57) ABSTRACT

A radiographic imaging apparatus includes an imaging means which captures a radiation image based on a radiation pulse emitted from a radiation generator, a radiation pulse detection means which detects the radiation pulse, and a control means which controls the imaging means based on a detection result obtained by the radiation pulse detection means. The control means includes a computing unit which computes the pulse width and period of the radiation pulse based on the detection result obtained by the radiation pulse detection means, and controls the imaging means based on the pulse width and period of the radiation pulse which are computed by the computing unit.

19 Claims, 8 Drawing Sheets

RADIOGRAPHIC IMAGING APPARATUS AND SYSTEM, METHOD THEREFOR, AND PROGRAM

FIELD OF THE INVENTION

The present invention relates to a radiographic imaging apparatus and system which performs radiography using radiation or the like, a method therefor, and a program.

BACKGROUND OF THE INVENTION

FIG. 4 is a block diagram showing the schematic arrangement of a radiographic imaging system including a conventional radiographic imaging apparatus. FIG. 5 is a schematic circuit diagram of an imaging means used in conventional radiographic imaging apparatus. FIG. 6 is a timing chart showing the driving timing for a conventional radiographic imaging apparatus.

As shown in FIG. 4, a conventional radiographic imaging system 400 includes a radiation generator 401, an imaging means 402, a radiation I/F 403, and a control means 404 (see, for example, Japanese Patent Laid-Open No. 08-130682 and U.S. Pat. Nos. 5,677,940 and 6,515,286). The imaging means 402 is connected to the control means 404 via cable 405c. Control signals such as driving pulses are supplied from the control means 404 to the imaging means 402. The radiation generator 401 and the control means 404 are connected to each other through the radiation I/F 403. The radiation generator 401 and the radiation I/F 403 are connected to each other via the cable 405b. The radiation I/F 403 and control means 404 are connected to each other via the cable 405a.

As shown in FIG. 5, the imaging means 402 used in conventional radiographic imaging apparatus has an area sensor 501 performing matrix driving, which has a two-dimensional array of pixels each comprising a photoelectric conversion element such as a p-i-n photodiode formed by using amorphous-silicon and a switching element such as a thin-film transistor (TFT) (see, for example, U.S. Pat. No. 5,079,426). A bias voltage Vs is applied from a power supply to the common electrode side of the p-i-n photodiode of each pixel. The gate electrode of the TFT of each pixel is connected to a corresponding one of the common gate lines Vg1 to Vg3. The common gate lines are connected to a gate driver 502 comprising shift registers and the like (not shown). The source electrode of each TFT is connected to a corresponding one of the common data lines Sig1 to Sig3. A reading unit 503 which outputs an image signal comprises input amplifiers 504, sample and hold circuits 505, an analog multiplexer 506, an output amplifier 507, and the like.

The operation of the conventional radiographic imaging system 400 will be described next with reference to the timing chart of FIG. 6. Referring to FIG. 6, signals RES, Vg1, Vg2, Vg3, and SMPL are control signals to be supplied from the control means 404 to the imaging means 402 in FIG. 4. These signals are also shown in FIG. 5. In this case, the signal RES is used to reset the common data lines and the input amplifiers 504, the signals Vg1 to Vg3 are applied to the gates of the TFTs connected to the respective common gate lines, and the signal SMPL is used to transfer charges to the capacitors of the sample and hold circuits 505. An analog output is an output signal which is output from the reading unit 503 and contains the information of an object.

The conventional radiographic imaging system 400 supplies control signals to the radiation generator 401 and imaging means 402 by using the common control means 404 to make the radiation generator 401 and imaging means 402 operate synchronously. This makes it possible to synchronize a radiation control signal A supplied from the control means 404 to the radiation I/F 403 with a radiation control signal C supplied from the control means 404 to the imaging means 402.

However, since a device such as a relay is used for the radiation I/F 403, a timing delay occurs. For this reason, in some case, the radiation control signal A is supplied, as a radiation control signal B obtained by delaying the signal A by a predetermined interval (e.g., an interval D in FIG. 6), to the radiation generator 401. In this case, the radiation generator 401 generates pulse-like radiation to the imaging means 402 in accordance with the radiation control signal B obtained by delaying the radiation control signal A by a predetermined interval.

In radiographic imaging system based on pulse radiation emissions, radiation emissions can be inhibited during read intervals A-B and A'-B' of FIG. 6. For this reason, the control means 404 needs to supply the control signals RES, Vg1, Vg2, Vg3, and SMPL and the like to the imaging means 402 upon setting a timing margin in consideration of the delay of the above radiation pulse and the like.

In addition, the relay device used for the radiation I/F has a large delay and is unstable, and hence it is difficult to perform accurate timing control. That is, a timing limitation tends to occur. Because of this limitation, high-speed reading is inevitably required. As a consequence, some disadvantageous effects may occur in terms of the noise band.

Also available is a method of image capturing by irradiating an object with continuous radiation without synchronizing the radiographic imaging apparatus with the imaging means. In this method, however, an image of a moving object blurs and this results in a deterioration of the image quality.

SUMMARY OF THE INVENTION

The present invention has been made in consideration of the above problems, and has as its object to provide a radiographic imaging apparatus and system which can more reliably make a radiation generator and an imaging means operate synchronously.

In order to achieve the above object, according to a first aspect of the present invention, there is provided a radiographic imaging apparatus comprising an imaging means which captures a radiation image based on a radiation pulse emitted from a radiation generator, a radiation pulse detection means which detects the radiation pulse, and a control means which controls the imaging means based on a detection result obtained by the radiation pulse detection means, wherein the control means includes a computing unit which computes a pulse width and period of the radiation pulse based on the detection result obtained by the radiation pulse detection means, and controls the imaging means based on the pulse width and period of the radiation pulse which are computed by the computing unit. In this case, control performed by the control means with respect to the imaging means includes, for example, causing each of pixels arrayed in a lattice form in the imaging means to output a control signal for reading out a pixel signal corresponding to the amount of radiation received. In addition, the radiation pulse is emitted from the radiation generator.

According to a second aspect of the present invention, there is provided a radiographic imaging system comprising a radiation generator, and the above radiographic imaging apparatus.

According to a third aspect of the present invention, there is provided a radiographic method comprising an irradiation step of irradiating an imaging means, which captures a radiation image, with a radiation pulse, a detecting step of detecting the radiation pulse, and a control step of controlling the imaging means based on a detection result obtained in the detecting step, wherein in the control step, the pulse width and the period of the radiation pulse are computed based on the detection result obtained in the detecting step, and the imaging means is controlled based on the computed pulse width and period of the radiation pulse.

According to a fourth aspect of the present invention, there is provided a program for causing a computer to execute the above radiographic method.

According to a fifth aspect of the present invention, there is provided a computer-readable storage medium storing the above program.

This arrangement makes it possible to more reliably synchronize the timing of a radiation pulse emitted from the radiation generator with the timing of the image capturing operation of the imaging means without requiring any cumbersome connection with the radiation generator which emits a radiation pulse or providing any interface as in the prior art.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate an embodiment of the invention and, together with the description, serve to explain the principles of the invention.

DETAILED DESCRIPTION OF THE PREFERRED EMBODIMENT

A preferred embodiment of the present invention will be described below with reference to the accompanying drawings. This embodiment will exemplify X-rays as radiation. However, the present invention is not limited to this, and radiation includes α rays, β rays, and γ rays.

Figure 1:
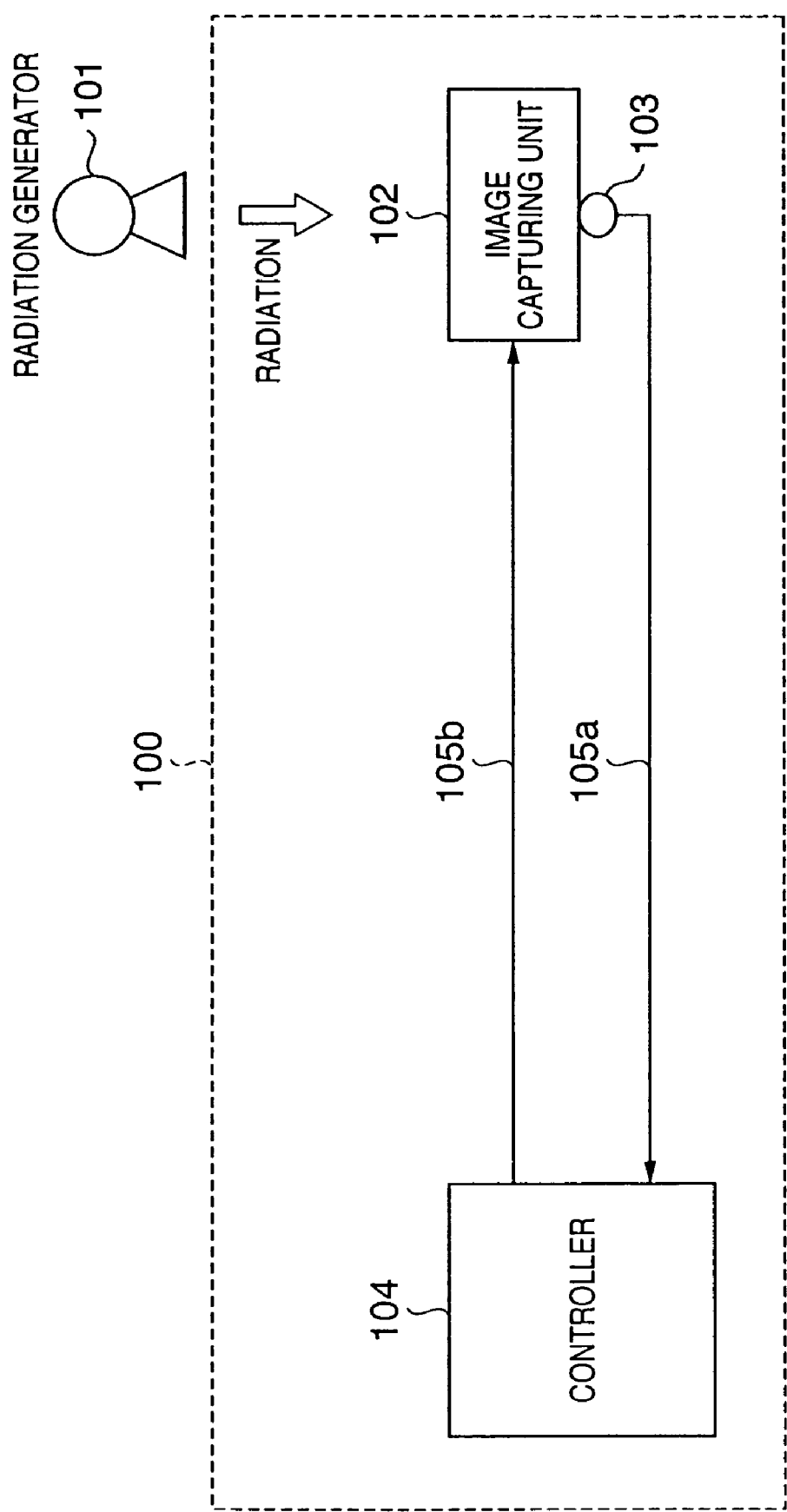
FIG. 1 is a block diagram showing the schematic arrangement of a radiographic imaging apparatus according to a preferred embodiment of the present invention.

FIG. 1 is a view showing the schematic arrangement of a radiographic imaging apparatus according to a preferred embodiment of the present invention.

Referring to FIG. 1, reference numeral 100 denotes a radiographic imaging apparatus, which includes an imaging means 102, a radiation pulse detection means 103, and a control means 104. A radiation generator 101 irradiates the imaging means 102 of the radiographic imaging apparatus 100 with pulse-like radiation (to be referred to as a radiation pulse hereinafter). In this manner, a radiographic imaging system including the radiographic imaging apparatus 100 and radiation generator 101 is formed. The imaging means 102 captures a radiation image by detecting the intensity of radiation emitted from the radiation generator 101 at a timing corresponding to a control signal from the control means 104. The radiation pulse detection means 103 detects a change in radiation pulse emitted from the radiation generator 101, and outputs a detection signal to the control means 104.

Figure 4:
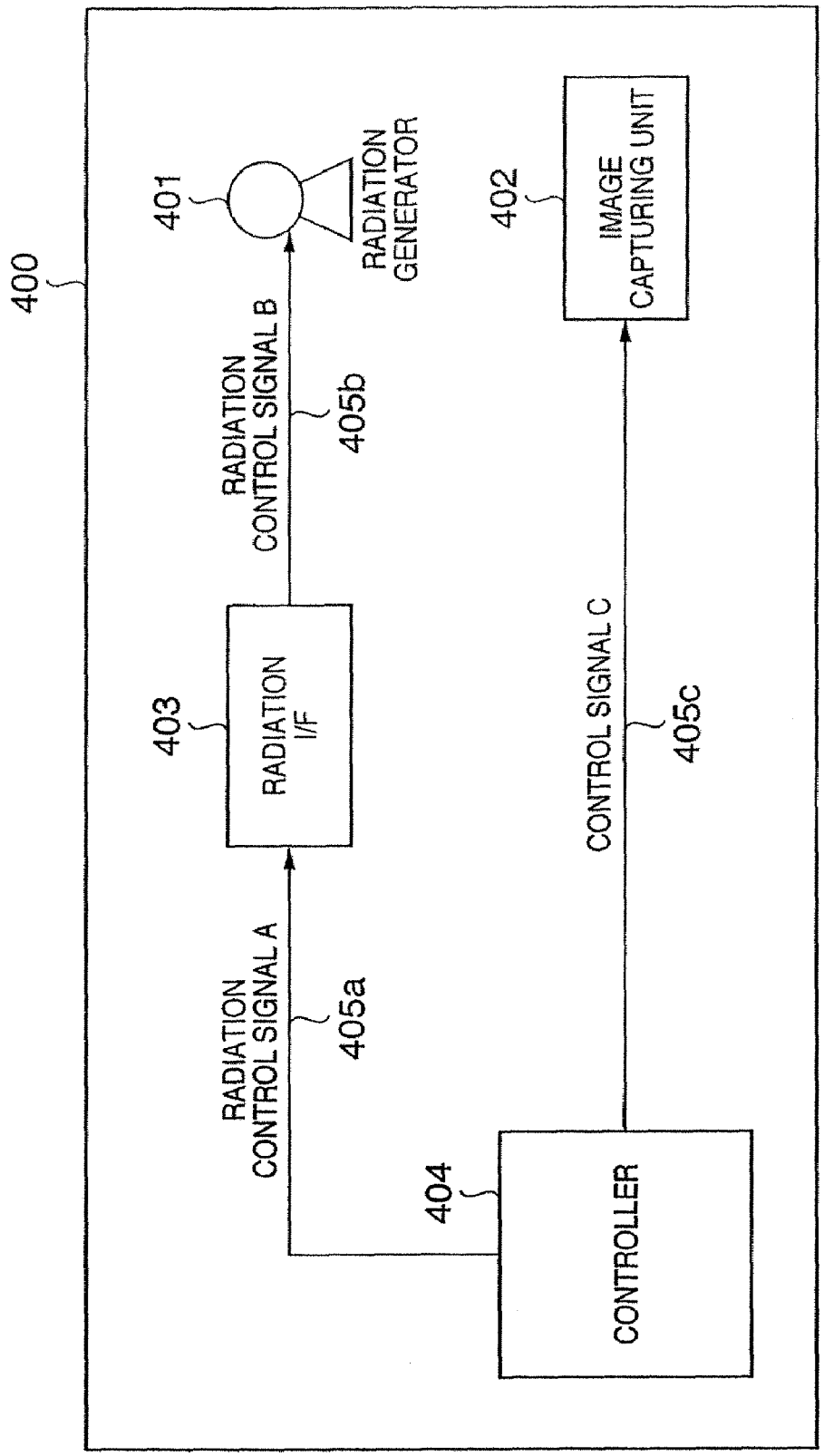
FIG. 4 is a block diagram showing the schematic arrangement of a radiographic imaging system including a conventional radiographic imaging apparatus.

As compared with the conventional radiographic imaging system shown in FIG. 4, the radiographic imaging system according to this embodiment has at least the following characteristics different from those of the conventional radiographic imaging system.

First of all, in the radiographic imaging system according to this embodiment, the radiation generator 101 is not connected to the control means 104 of the radiographic imaging apparatus 100 via a cable, and there is no need to communicate between them. In addition, the radiographic imaging system according to this embodiment is provided with the radiation pulse detection means 103. A detection signal which is output from the radiation pulse detection means 103 and indicates a change in radiation pulse is input to the control means 104. The control means 104 can control the imaging means 102 based on the detection result obtained by the radiation pulse detection means 103. For example, the radiation pulse detection means 103 comprises a phototimer including a p-i-n photodiode formed by using crystalline silicon, and can accurately detect the leading and trailing edges of a radiation pulse emitted from the radiation generator 101. In this embodiment, the radiation pulse detection means 103 and control means 104 are connected to each other, and the control means 104 and imaging means 102 are connected to each other via cables 105a and 105b. In the preferred embodiment of the present invention, such connection is not limited to that using a cable, and wireless communication such as a wireless LAN or infrared communication may be used.

A detailed arrangement of the imaging means 102 shown in FIG. 1 will be described next.

Figure 3:
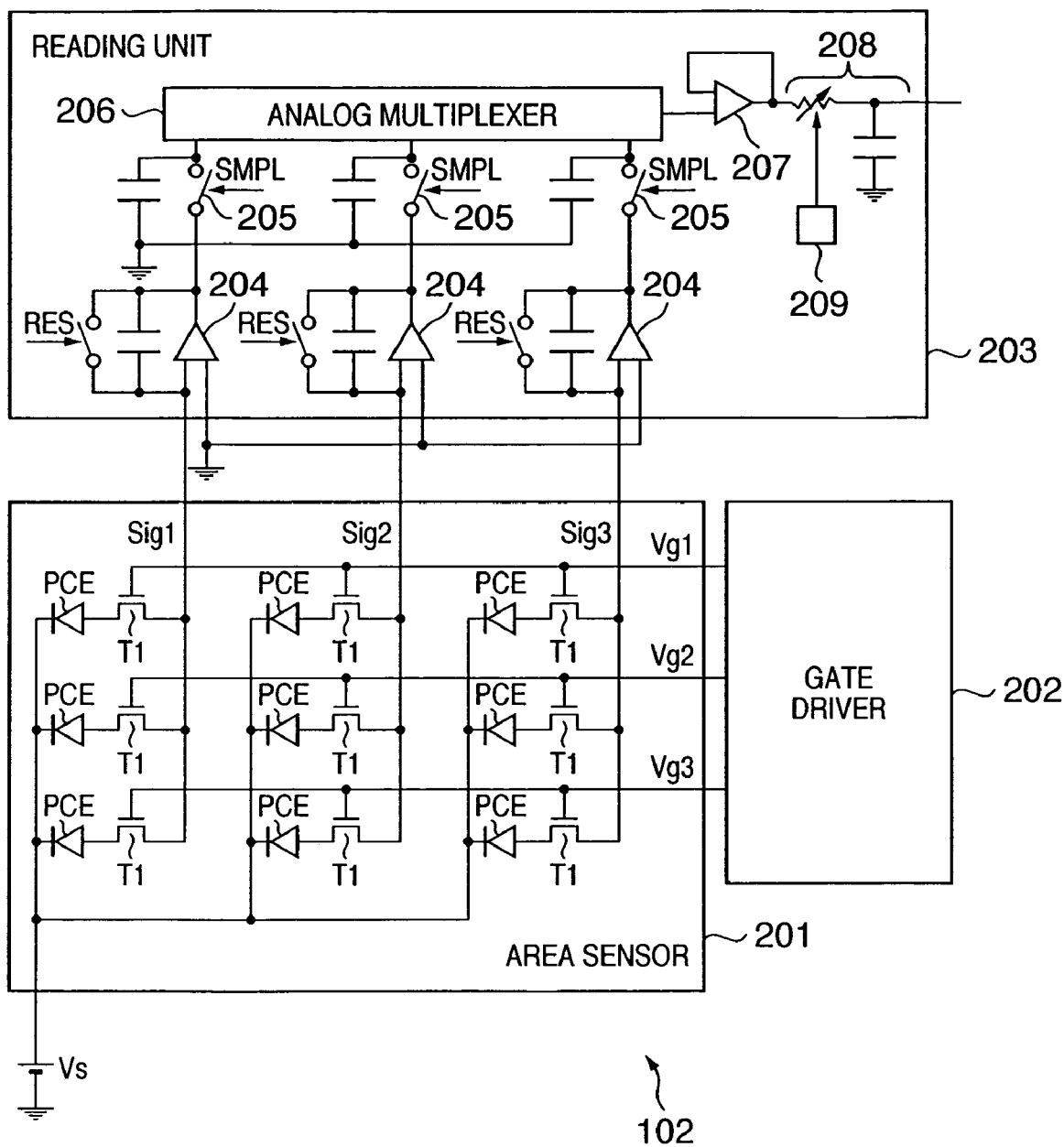
FIG. 3 is a circuit diagram showing a detailed arrangement of the imaging means 102 shown in FIG. 1.

FIG. 3 is a view showing a detailed arrangement of the imaging means 102 shown in FIG. 1. Referring to FIG. 3, an area sensor 201 has a two-dimensional array of pixels each comprising a photoelectric conversion element (PCE) such as a p-i-n photodiode formed by using amorphous silicon and a switching element such as a thin-film transistor (TFT), and performs matrix driving. A bias voltage Vs is applied from a power supply to the common electrode side of a p-i-n photodiode of each pixel of the area sensor 201. The gate electrode of a TFT T1 of each pixel is connected to a corresponding one of common gate lines Vg1 to Vg3. The common gate lines Vg1 to Vg3 are connected to a gate driver 202. The gate driver 202 comprises, for example, shift registers and the like.

The source electrode of each TFT T1 is connected to a corresponding one of common data lines Sig1 to Sig3, and outputs a pixel signal to a reading unit 203. The reading unit 203 includes input amplifiers 204, sample and hold circuits 205, an analog multiplexer 206, an output amplifier 207, an LPF circuit 208, and a resistance control unit 209. The reading unit 203 generates an image signal based on pixel signals input from the common data lines Sig1 to Sig3, and outputs the signal as an analog signal.

Figure 5:
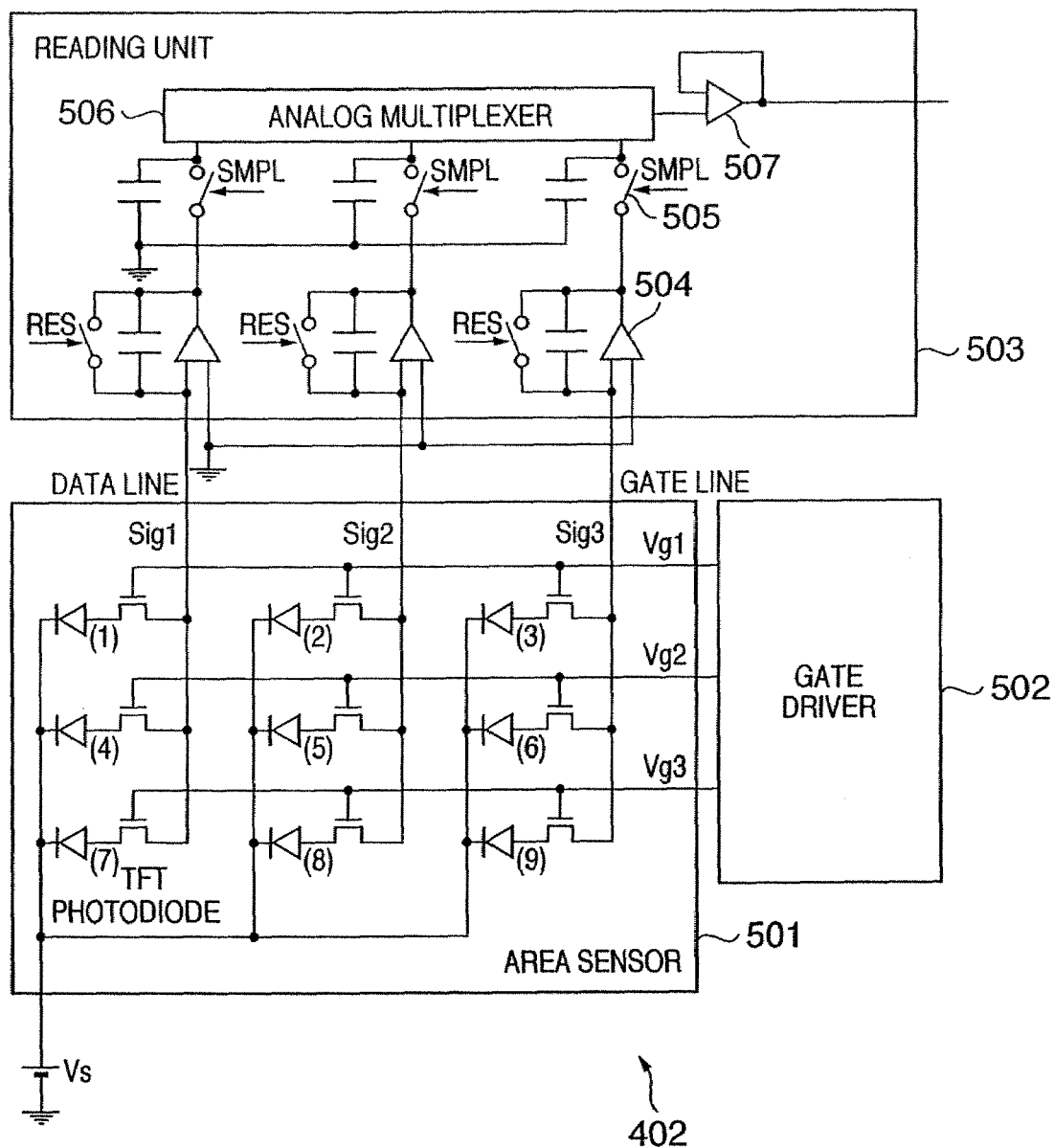
FIG. 5 is a schematic circuit diagram showing an imaging means used in a conventional radiographic imaging apparatus.

Characteristics of the imaging means 102 shown in FIG. 3 which differ from those of the conventional imaging means shown in FIG. 5 will be described. First of all, the differences are that the imaging means 102 has the low-pass filter (to be abbreviated as LPF) circuit 208 connected to the output amplifier 207 of the reading unit 203, and the LPF circuit 208 has a variable resistance, and that the resistance of the variable resistance circuit of the LPF circuit 208 can be changed under the control of the resistance control unit 209. With this arrangement, the cutoff frequency of the LPF circuit 208 connected to the output amplifier 207 of the reading unit 203 can be controlled by the resistance control unit 209. More specifically, the resistance control unit 209 operates in accordance with control signals from the control means 104 in FIG. 1. In other words, the control means 104 can control limitation processing for a frequency bandwidth with respect to an output signal from the imaging means 102. For example, the control means 104 can change the frequency bandwidth of the LPF circuit 208 in accordance with the driving speed of the area sensor 201. This can achieve a reduction in noise in an output signal from the imaging means 102. Note that in this embodiment, the area sensor has been described as being comprised of p-i-n photodiodes as photoelectric conversion elements formed by using amorphous silicon and TFTs as switching elements. However, the preferred embodiment of the present invention is not limited to this, and MIS sensors formed by using amorphous silicon may be used as photoelectric conversion elements instead of p-i-n photodiodes. When a radiographic imaging apparatus is to be formed, a scintillator as a wavelength converter which is made of cesium iodide or the like and converts radiation into light in a wavelength band which can be detected by a photoelectric conversion element. In this case, a conversion device is comprised of a photoelectric conversion element and scintillator. In addition, a conversion device may be formed by using a material which directly converts radiation into charge, e.g., lead iodide, mercury iodide, amorphous selenium, or gallium arsenide. Furthermore, the material for the area sensor using photoelectric conversion elements is not limited to amorphous silicon, and crystalline silicon may be used. When an area sensor is to be formed by using crystalline silicon, a conversion device such as a CCD or CMOS sensor can be used.

The operation of the imaging means 102 described with reference to FIG. 3 will be described.

Figure 2:
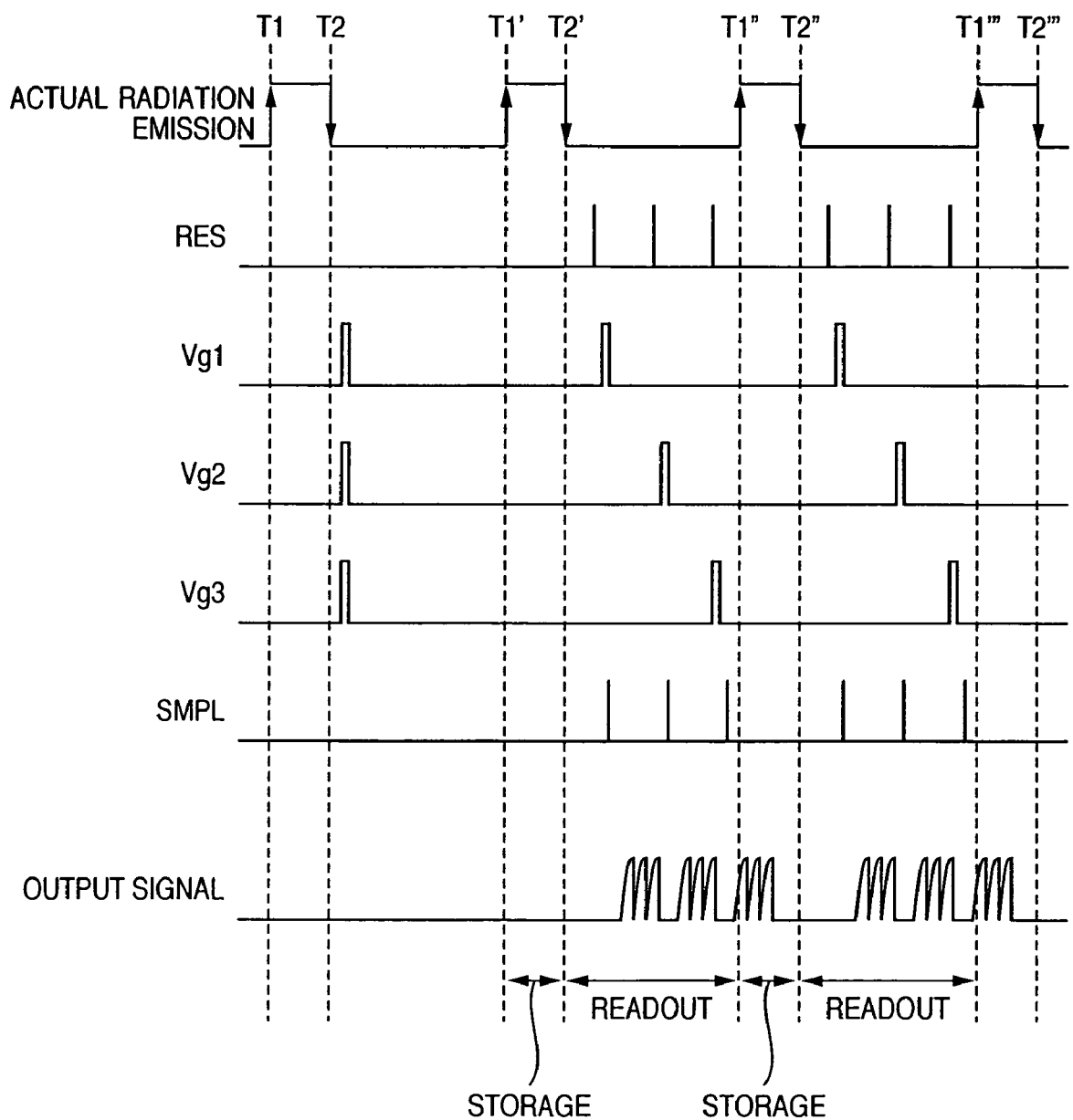
FIG. 2 is a timing chart showing the driving timing of an imaging means 102.

FIG. 2 is a timing chart showing the driving timing of the imaging means 102 described with reference to FIG. 3. As shown in FIG. 2, the radiation generator 101 of this embodiment periodically generates radiation pulses. The radiographic imaging apparatus 100 of this embodiment can continuously read out these radiation pulses. The radiation pulse detection means 103 detects a leading edge T1 of the first radiation pulse (actual radiation emission), a trailing edge T2 of the first radiation, a leading edge T1' of the next radiation pulse, and the like. Upon receiving this detection signal, the control means 104 has a function (computing function) of calculating the pulse width and period of radiation pulses from the radiation generator 101. The control means 104 then controls the driving of the imaging means 102 as shown in FIG. 2 based on the calculated pulse width and period of radiation pulses. More specifically, the control means 104 drives the imaging means 102 by supplying the control signals RES, Vg1, Vg2, Vg3, SMPL, and the like to the imaging means 102. For example, the control means 104 controls the frame rate of the imaging means 102 in accordance with the obtained pulse width and period of radiation pulses.

First of all, the control means 104 keeps the imaging means 102 in the storage stage during an interval T1'-T2' in which a radiation pulse is rising. The control means 104 then controls the driving speed so as to complete readout processing for pixel signals in the interval between a radiation pulse trailing edge timing T2' and a leading edge timing T1" of the next radiation pulse. That is, the control means 104 performs control to complete reset operation based on the signal RES, charge transfer operation based on the signals Vg1 to Vg3, and the sample/hold operation based on the signal SMPL in the interval between T2' and T1". In addition, the control means 104 changes the frequency bandwidth of the LPF circuit 208 connected to the output amplifier 207 of the reading unit 203 in accordance with the driving speed. This makes it possible to change the frequency bandwidth of the output amplifier 207 determined by the LPF circuit 208 in accordance with the driving speed, thereby achieving a reduction in noise in an output signal.

Figure 7:
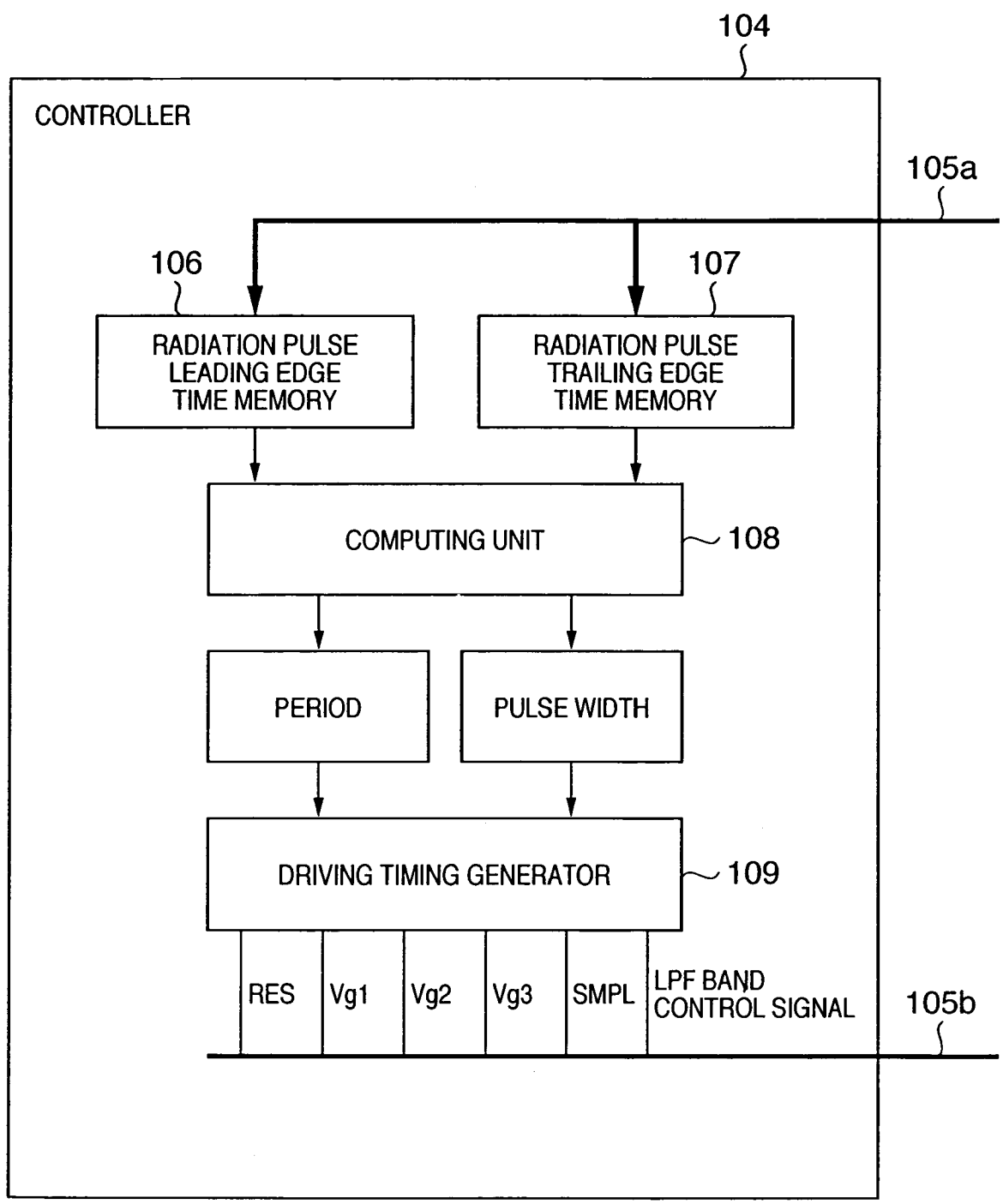
FIG. 7 is a block diagram showing a specific arrangement of a control means 104 according to a preferred embodiment of the present invention.

FIG. 7 shows a specific arrangement of the control means 104 of this embodiment. A radiation pulse leading edge time memory 106 and radiation pulse trailing edge time memory 107 sequentially store and update times T1, T1', T1", T1"', . . . , and T2, T2', T2", T2"', . . . shown in FIG. 2, and inputs them to a computing unit 108. The computing unit 108 calculates a pulse period and pulse width based on information from these memories, and causes a driving timing generator 109 to generate a signal for driving the area sensor. Referring to FIG. 7, the driving timing generator 109 generates signals RES, Vg1 to Vg3, SMPL, and an LPF bandwidth control signal. However, signals to be generated are not limited to these signals. For example, when the gate driver 202 is to be formed by using a shift register, a start pulse, shift clock, enable signal, and the like may be generated instead of the signals Vg1 to Vg3. In addition, in this embodiment, the control means 104 and imaging means 102 are separately provided. However, part or all of the function of the control means may be incorporated in the imaging means. In current medical fields, a portable imaging-means called a portable cassette is sometimes used. It is therefore more preferable to incorporate part or all of the function of the control means 104 in the imaging means 102.

The radiographic imaging apparatus 100 performs the above processing for radiation pulses in an interval T1"-T2" and radiation pulses in an interval T1"'-T2"'. The radiographic imaging apparatus 100 in this embodiment can read out a radiation image by driving the imaging means 102 in synchronism with a radiation pulse emitted from the radiation generator 101 without connecting the control means 104 and radiation generator 101 using a cable or the like. That is, a cable and radiation I/F for the connection between the radiation generator 101 and the control means 104, which have been required, become unnecessary, and hence a radiographic imaging system can be formed more simply. The radiographic imaging apparatus 100 of this embodiment is compatible with radiation generators which differ in specifications depending on the makers unlike a conventional apparatus with a radiation I/F which cannot sometimes cope with such radiation generators.

An arrangement like that of the radiographic imaging apparatus 100 of this embodiment can eliminate the necessity of cumbersome cable connection with the radiation generator 101, and hence can be suitably applied to a portable radiographic imaging apparatus. In this embodiment, the radiation pulse detection means 103 is provided near the imaging means 102. However, the radiation pulse detection means 103 may be provided near the radiation generator 101 or near an object. In addition, the radiation pulse detection means 103 may be provided in the imaging means 102. Alternatively, a radiation pulse may be detected by using at least part of an output from the imaging means 102.

Figure 8:
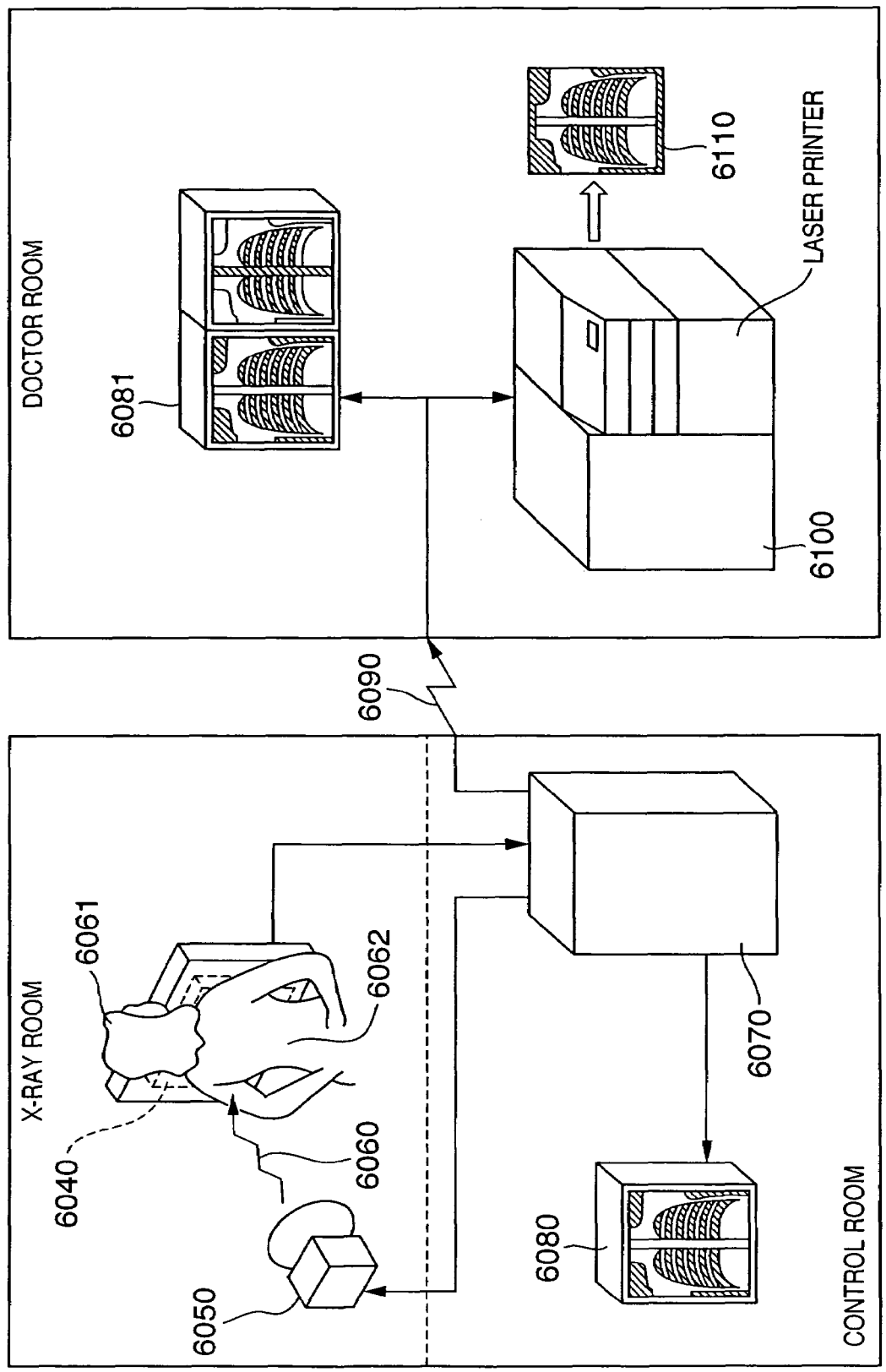
FIG. 8 is a view showing a radiographic imaging system using a radiographic imaging apparatus according to the preferred embodiment of the present invention.

FIG. 8 is a view showing a radiographic imaging system using the radiographic imaging apparatus according to the preferred embodiment of the present invention. Reference numeral 6040 denotes a portable image capturing apparatus; 6050, a mobile radiation generator; 6060, radiation emitted from the mobile radiation generator 6050; 6061, a patient or subject to be examined; 6062, a chest portion of the patient or subject to be examined; 6070, an image processor which performs image processing of an electrical signal from the image capturing apparatus 6040; 6080, a display which displays the image information having undergone image processing; 6090, a transmission unit such as a telephone line for transmitting image information; and 6100, a developing unit such as a film processor for outputting image information to a film 6110. A radiation pulse detection means is preferably incorporated in the portable image capturing apparatus 6040. Alternatively, part or all of the function of the control means 104 may be incorporated in the image processor 6070 or image capturing apparatus 6040. It is more preferable in terms of portability that the function of the control means 104 be incorporated in the portable image capturing apparatus 6040.

Figure 6:
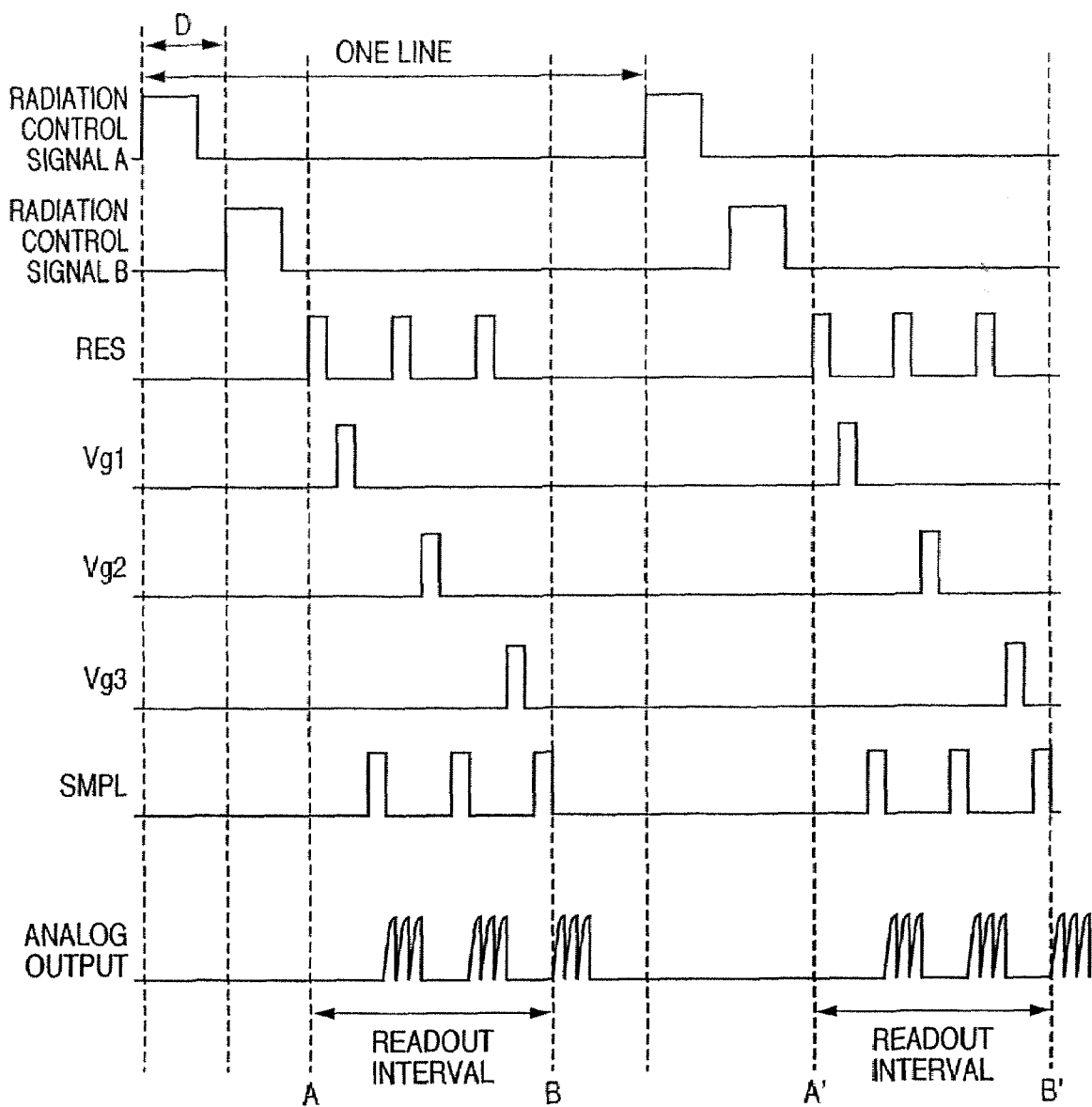
FIG. 6 is a timing chart showing the driving timing of the conventional radiographic imaging apparatus.

In the radiographic imaging apparatus 100 according to this embodiment, since no delay like that in the interval D shown in FIG. 6 as in the prior art occurs with respect to the timing of periodic radiation pulses output from the radiation generator 101, timing limitations are reduced, and there is no need to perform high-speed readout operation in the imaging means 102 as in the prior art. This makes it possible to ensure a sufficient time for storage and readout operation of pixel signals, and hence to provide a radiographic imaging apparatus which can capture a radiation image with a higher S/N ratio (lower noise) than the conventional apparatus. In addition, in the radiographic imaging system of this embodiment, since no radiation I/F is used, there is no chance that a timing error will be caused by a large delay in a radiation I/F (relay device) as in the prior art. Furthermore, according to the arrangement of the control means 104 of this embodiment, the driving of the imaging means can be controlled in real time by computing a pulse period and pulse width in real time. In some case, the pulse period and pulse width of the radiation generator used for diagnosis change depending on the characteristics of the generator or in the process of diagnosis. According to the preferred embodiment of the present invention, since the driving of the imaging means can be changed in real time, changes in the above pulse period and pulse width of the radiographic imaging apparatus can be coped with. This improves operability.

In the above embodiment, the computing function and the like of the control means 104 is realized by hardware. However, the present invention is not limited to this. Each processing function may be realized by reading out a program for implementing the function and causing a CPU (Central Processing Unit) to execute it. That is, the hardware arrangement of the control means 104 may include at least a CPU and memory.

In addition, the preferred embodiment of the present invention is not limited to the above arrangement, and at least some of the functions for the respective processes in the control means 104 may be implemented by single purpose hardware. The above memory is typically a computer-readable recording medium, including, for example, a nonvolatile memory such as a flash memory, a ROM, and the like. However, this memory may comprise a magnetooptical disk device, an HDD (Hard Disk Drive), a read-only recording medium such as a CD-ROM, a nonvolatile memory other than a RAM, or a computer-readable/writable recording medium obtained by combining them.

In addition, each process may be performed by recording a program for implementing each function of the control means 104 on a computer-readable recording medium and causing a computer system to read in the program recorded on the recoding medium and execute it. Note that the computer system can include hardware such as peripheral devices as well as software such as an OS. More specifically, the present invention incorporates a case wherein the functions of the above-described embodiment are realized when the programs read out from the storage medium are written in the memory of a function expansion board inserted into the computer or a function expansion unit connected to the computer, and the CPU of the function expansion board or function expansion unit performs part or all of actual processing based on the instructions of the program codes.

The computer-readable recording medium typically includes portable media such as a flexible disk, magnetoopical disk, ROM, and CD-ROM and storage devices such as a hard disk incorporated in a computer system. However, the computer-readable recording medium may also include a memory designed to hold a program for a predetermined period of time, like a nonvolatile memory (RAM) in a computer system serving as a server or client when the program is transmitted through a network such as the Internet or a-communication circuit such as a telephone line.

The above program may be transmitted from a computer system having the program stored in a storage device or the like to another computer system through a transmission medium or a transmission wave in a transmission medium. In this case, the transmission medium which transmits the program includes a medium having a function of transmitting information like a network (communication network) such as the Internet or a communication circuit (communication line) such as a telephone line.

The above program may be one that implements part of the above functions. Furthermore, the program may be a so-called difference file (difference program), which can implement the above function in combination with the program which has already been recorded on the computer system.

In addition, a program product such as a computer-readable recording medium on which the above program is recorded can be applied as an embodiment of the present invention. The above program, recording medium, transmission medium, and program product are incorporated in the present invention.

The embodiment of the present invention has been described in detail above with reference to the accompanying drawings. However, the specific arrangement of the present invention is not limited to this embodiment, and includes a modification of the embodiment within the spirit and scope of the invention.

As many apparently widely different embodiments of the present invention can be made without departing from the spirit and scope thereof, it is to be understood that the invention is not limited to the specific embodiments thereof except as defined in the claims.

CLAIM OF PRIORITY

This application claims priority from Japanese Patent Application No. 2004-290655 filed Oct. 1, 2004, which is hereby incorporated by reference herein.

What is claimed is:

1. A radiographic imaging apparatus comprising:
an imaging unit which captures a radiation image based on a radiation pulse emitted from a radiation generator, wherein said imaging unit includes an area sensor which has a two-dimensional array of pixels and a reading unit which generates an image signal based on pixel signals from the pixels;
a radiation pulse detection unit which detects the radiation pulse; and
a control unit which controls said imaging unit based on a detection result obtained by said radiation pulse detection unit,
wherein said control unit includes a computing unit which computes a pulse width and period of the radiation pulse based on the detection result obtained by said radiation pulse detection unit, and controls said imaging unit based on the pulse width and period of the radiation pulse which are computed by said computing unit such that said control unit completes readout processing by said reading unit within one period of the radiation pulse.

2. The apparatus according to claim 1, wherein said reading unit includes a sample and hold circuit, and said control unit controls a frame rate of said imaging unit based on the pulse width and period which are computed by said computing unit such that said control unit completes a sample and hold operation by said sample and hold circuit within one period of the radiation pulse.

3. The apparatus according to claim 2, wherein
said imaging unit includes a filter which limits a specific frequency bandwidth of an output signal from said imaging unit, and
said control unit outputs a control signal for limiting the specific frequency bandwidth to said filter based on the pulse width and period computed by said computing unit.

4. The apparatus according to claim 1, wherein said control unit controls said imaging unit in real time based on the pulse width and period of the radiation pulse which are computed by said computing unit in real time.

5. The apparatus according to claim 1, wherein said radiation pulse detection unit is provided as part of said imaging unit.

6. The apparatus according to claim 1, wherein said radiation pulse detection unit detects a change timing of the radiation pulse by using an output signal from said imaging unit.

7. The apparatus according to claim 1, wherein said imaging unit is a portable cassette which includes said radiation pulse detection unit and said control unit.

8. The apparatus according to claim 1, wherein each of said pixels comprising a photoelectric conversion element and a switching element.

9. The apparatus according to claim 8, wherein said photoelectric conversion element is a p-i-n photodiode formed by using amorphous silicon.

10. The apparatus according to claim 8, wherein said photoelectric conversion element is a MIS sensor formed by using amorphous silicon.

11. The apparatus according to claim 8, wherein said photoelectric conversion element is formed by using a material which directly converts radiation into charge.

12. The apparatus according to claim 11, said material is selected from the group consisting of lead iodide, mercury iodide, amorphous selenium, and gallium arsenide.

13. The apparatus according to claim 8, wherein said switching element is formed by using amorphous-silicon.

14. The apparatus according to claim 1, wherein said area sensor is a CCD sensor formed by using crystalline silicon.

15. The apparatus according to claim 1, wherein said area sensor is a CMOS sensor formed by using crystalline silicon.

16. A radiographic imaging system comprising:
a radiation generator; and
a radiographic imaging apparatus defined in claim 1.

17. The system according to claim 16, wherein said imaging unit is a portable imaging unit and said radiation generator is a mobile radiation generator.

18. A radiographic method comprising steps of:
irradiating an imaging unit, which captures a radiation image, with a radiation pulse, wherein said imaging unit includes an area sensor which has a two-dimensional array of pixels and a reading unit which generates an image signal based on pixel signals from the pixels;
detecting the radiation pulse;
controlling the imaging unit based on a detection result obtained in the detecting step; and
reading out pixel signals from the pixels by said reading unit,
wherein in the control step, a pulse width and period of the radiation pulse are computed based on the detection result obtained in the detecting step, and the imaging unit is controlled based on the computed pulse width and period of the radiation pulse such that said control unit completes readout processing by said reading unit within one period of the radiation pulse.

19. A computer-readable storage medium storing a program for causing a computer to execute a radiographic method defined in claim 18.

* * * * *